US012653378B2

(12) United States Patent
Luis et al.

(10) Patent No.: US 12,653,378 B2
(45) **Date of Patent: *Jun. 16, 2026**

(54) UTILIZATION INDICATORS FOR SINGLE-USE VALVES FOR MEDICAL DEVICES

(71) Applicant: Boston Scientific Scimed, Inc., Maple Grove, MN (US)

(72) Inventors: Brian Luis, Boylston, MA (US); Nathan T. Cummings, Worcester, MA (US); Ryan Vincent William Pollock, Sterling, MA (US); Pauline R. Limberg, Northborough, MA (US); Kyle Patrick Moore, Milton, GA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/934,997

(22) Filed: Nov. 1, 2024

(65) Prior Publication Data

US 2025/0057394 A1        Feb. 20, 2025

Related U.S. Application Data

(63) Continuation of application No. 17/480,864, filed on Sep. 21, 2021, now Pat. No. 12,161,293.

(60) Provisional application No. 63/084,863, filed on Sep. 29, 2020, provisional application No. 63/084,869, filed on Sep. 29, 2020.

(51) Int. Cl.
*A61B 1/00*          (2006.01)
*A61B 1/015*         (2006.01)

*A61M 39/22*         (2006.01)
*F16K 37/00*         (2006.01)

(52) U.S. Cl.
CPC .......... *A61B 1/00068* (2013.01); *A61B 1/015* (2013.01); *A61M 39/22* (2013.01); *F16K 37/0008* (2013.01); *A61M 2205/584* (2013.01)

(58) Field of Classification Search
CPC . A61B 1/00068; A61B 1/015; A61B 1/00062; A61B 1/125; A61B 1/122; A61B 1/00103; A61B 1/121; A61B 2090/701; A61B 90/70; A61M 39/22; A61M 2205/584; A61M 2205/273; A61M 2039/224; F16K 37/0008
See application file for complete search history.

(56) References Cited

U.S. PATENT DOCUMENTS

2017/0067586 A1 *   3/2017   Jones ................. A61M 39/1011
2020/0146934 A1 *   5/2020   Werth ................... F16K 5/0414

* cited by examiner

*Primary Examiner* — Patrick C Williams
(74) *Attorney, Agent, or Firm* — Seager, Tufte & Wickhem, LLP

(57) ABSTRACT

The cleaning valves (or valves) of the current disclosure are generally single-use devices (SUDs) and therefore disposable. Reusing SUDs can be disadvantageous, as single-use devices are not designed to be reusable. Accordingly, valves for medical devices, such as endoscopes, disclosed may be configured to transition from a first state to a second state for indication of utilization of the valve, e.g., via exposure to a valve well. The transition from the first state to the second state may prevent reuse valves of the present disclosure. In embodiments, the valve may be made from a limited number of components and materials.

20 Claims, 12 Drawing Sheets

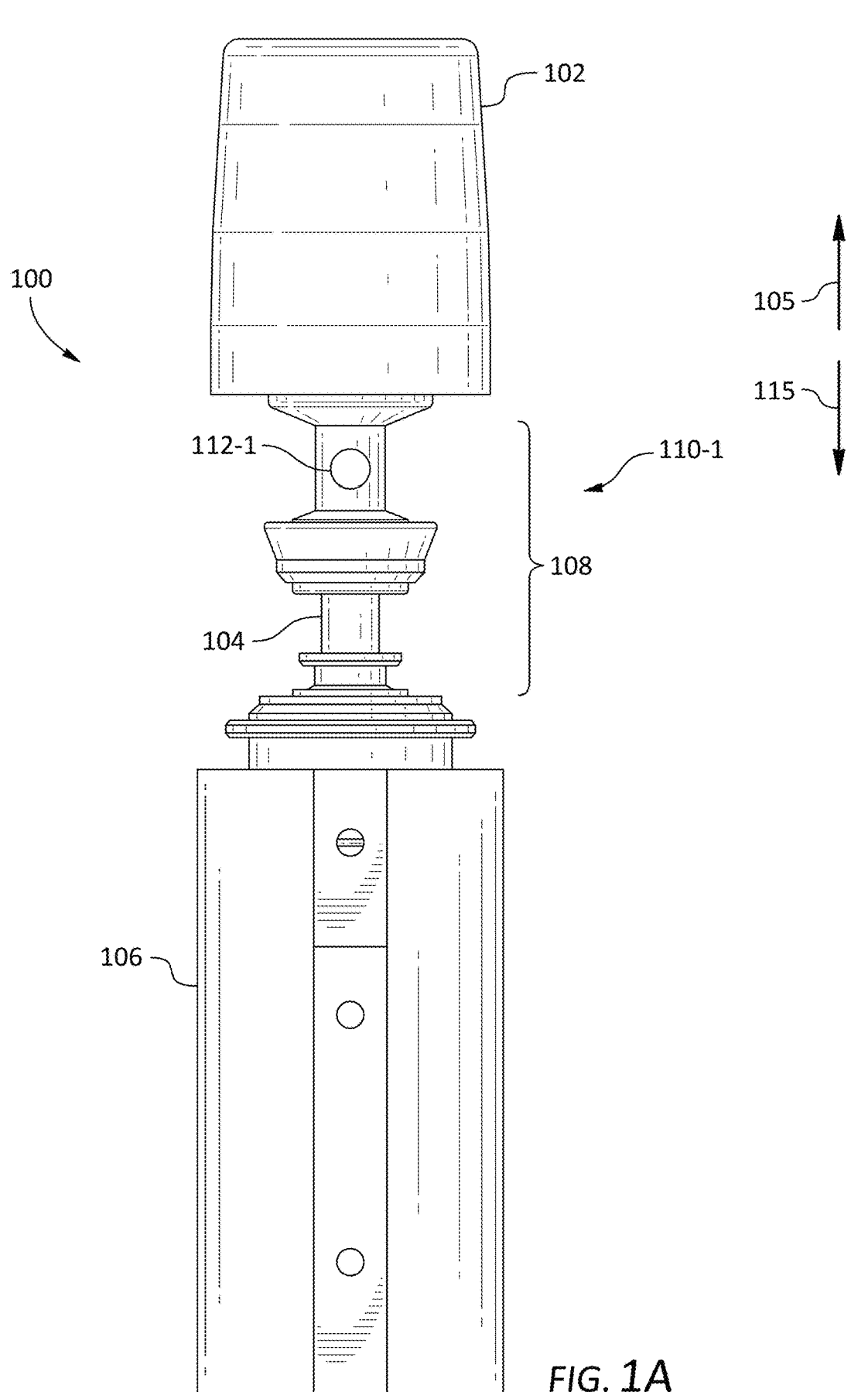
*FIG.* 1A 110-2

108

310-1
308
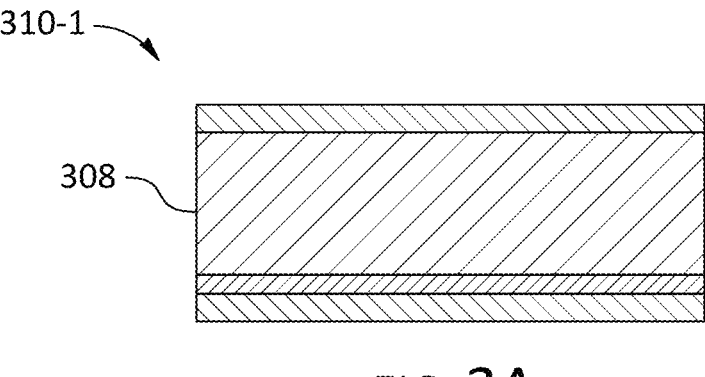
*FIG.* 3A
310-2
308
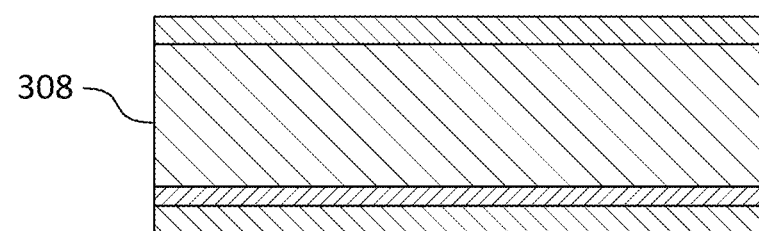
*FIG.* 3B
310-3
308
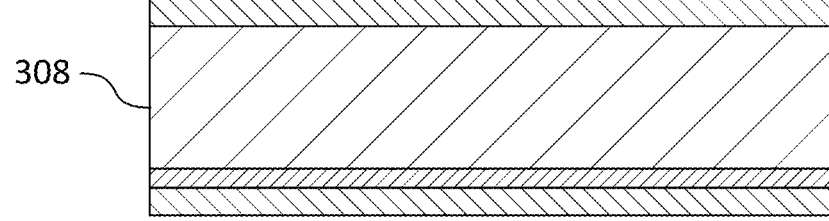
*FIG.* 3C 410-1
408
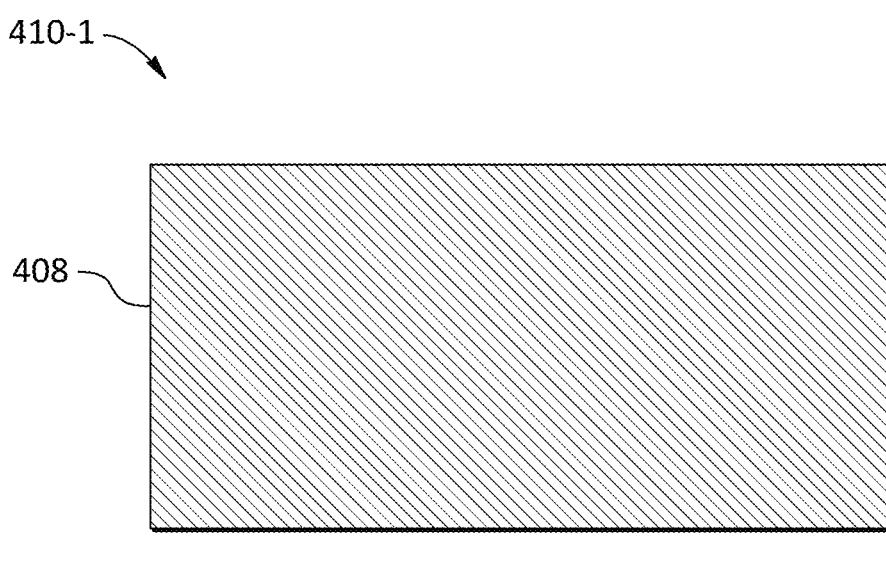
*FIG.* 4A
410-2
408
*FIG.* 4B

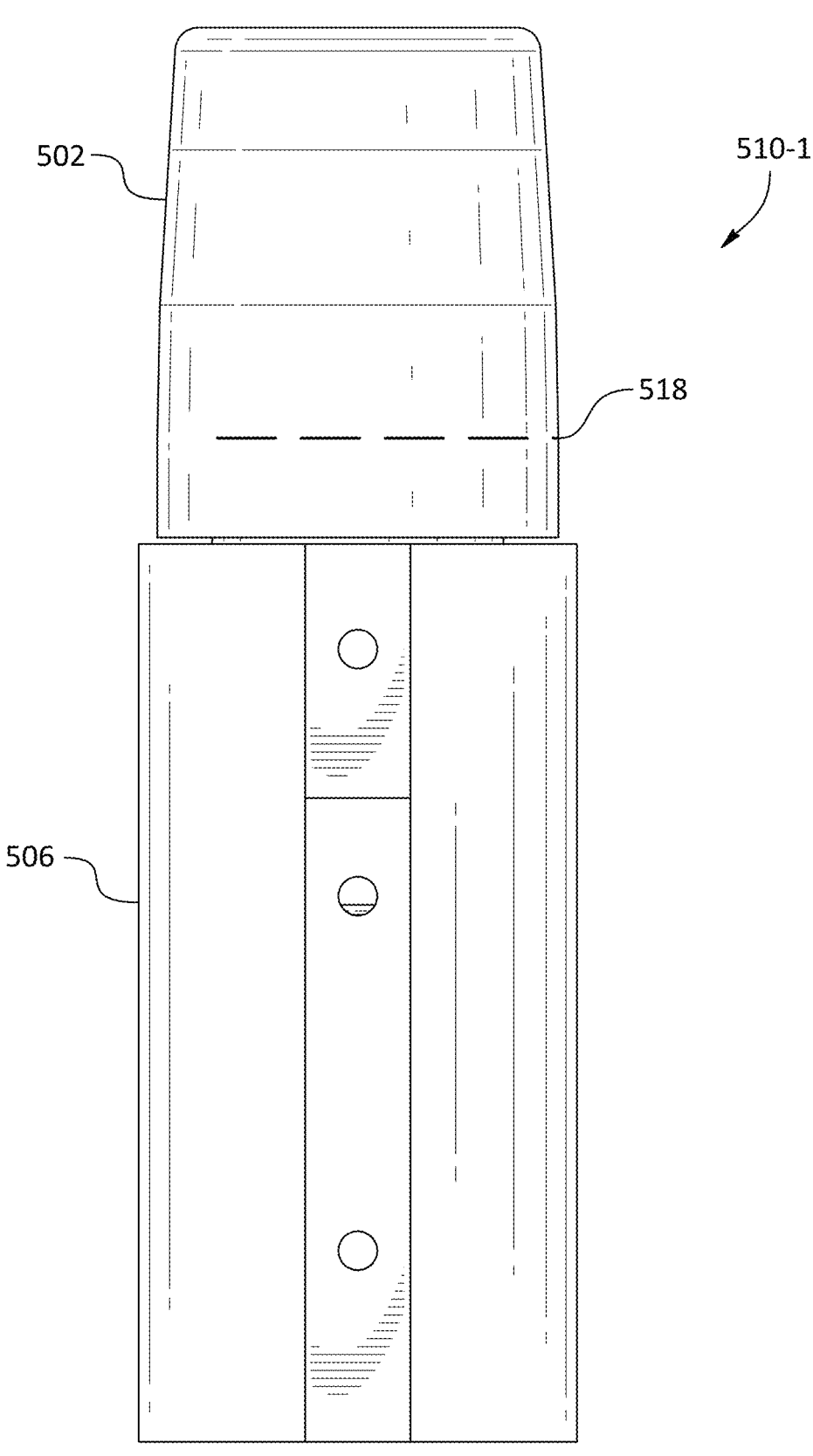
502
510-1
518
506
*FIG.* 5A 710-1
740-1
740-2
740-3
740-4
702
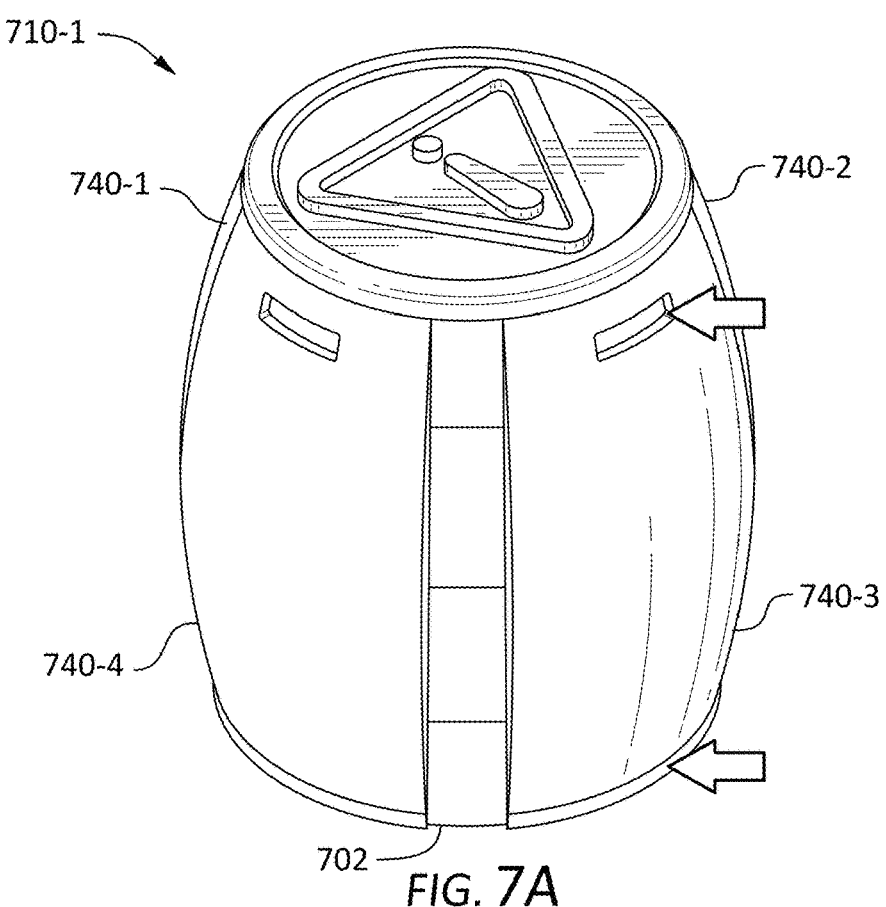
*FIG.* 7A
710-1
714
740-1
740-3
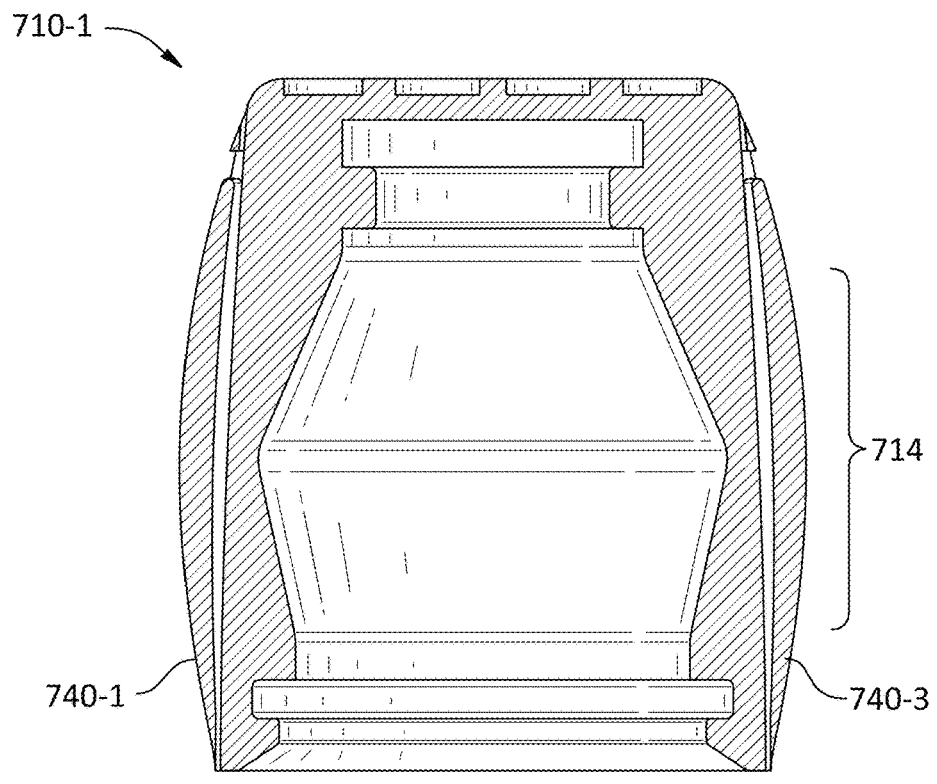
*FIG.* 7B

UTILIZATION INDICATORS FOR SINGLE-USE VALVES FOR MEDICAL DEVICES

PRIORITY

This application is a continuation of U.S. patent application Ser. No. 17/480,864, filed Sep. 21, 2021, which claims the benefit of priority under 35 U.S.C. § 119 to U.S. Provisional Application Ser. Nos. 63/084,869 and 63/084,863, each filed Sep. 29, 2020, the disclosures of which are incorporated herein by reference in their entirety.

FIELD

The present disclosure relates generally to valves for medical devices. In particular, the present disclosure relates to cleaning valves for medical devices

BACKGROUND

Endoscopes include functionality to deliver fluids and suction at a site of a procedure. Tubing for delivering fluids and/or suction extends from a handle of the endoscope, through a shaft of the endoscope, and to a distal tip of the endoscope. During a procedure, body fluids, tissues, or other material can build up in the tubing. In order to aid in reprocessing of reusable endoscopes between procedures, pre-processing is performed in an endoscopy suite. For example, water or other fluids are flushed through the tubing after the endoscope is removed from a patient, in order to clear debris from the air/water and/or suction tubing. The cleaning valve may be inserted into an air/water valve cylinder (i.e., valve well) of an endoscope after the scope is removed from a patient and the procedure valve is removed from the valve cylinder. An operator may then depress a button of the cleaning valve for a predetermined amount of time to flush the air and/or water channels of the endoscope prior to further reprocessing of the endoscope. An aspect of a cleaning valve that it is not confused with a procedural valve and inadvertently used in place thereof during a procedure when the scope is inserted within a patient. It is with all of the above considerations in mind that the improvements of the present disclosure may be useful.

SUMMARY

In one aspect, the present disclosure relates to a medical device comprising an interface member, a valve stem, and an indicator. The valve stem may be removably couplable to the interface member and include two or more orifices and a lumen in fluid communication with first and second orifices of the two or more orifices. The indicator may be configured to transition from a first state to a second state for indication of utilization of the valve stem.

In some embodiments, the indicator is disposed on the interface member. In various embodiments, the indicator is disposed on the valve stem. In many embodiments, the interface member comprises an elastic section and the indicator is disposed on a portion of the elastic section. In many such embodiments, the elastic section comprises a biasing section configured to bias the valve stem into a predetermined position in a valve well. In several embodiments, the indicator comprises a mechanochromatic material. In one or more embodiments, the indicator transitions from the first state to the second state in response to exposing the indicator to a liquid. In some embodiments, the indicator changes colors to transition from the first state to the second state. In various embodiments, utilization of the valve stem comprises insertion of the valve stem into a valve well and removal of the valve stem from the valve well. In various such embodiments, the indicator transitions from the first state to the second state when the valve stem is removed from the valve well. In some such embodiments, the indicator comprises a perforation that separates to transition from the first state to the second state when the valve stem is removed from the valve well. In further such embodiments, the perforation may comprise a radial perforation on the interface member. In many embodiments, the indicator comprises a radial leg disposed on the interface member, the radial leg including first and second ends. In many such embodiments, the first and second ends of the radial leg are attached to the interface member in the first state. In further such embodiments, the first end may be detached from the interface and the second end maybe attached to the interface member in the second state.

In another aspect, the present disclosure relates to medical device comprising an interface member, a valve stem, and an indicator. The interface member may be removably couplable to the valve stem. The valve stem may include a first portion slidably coupled to a second portion, the second portion comprising two or more orifices and a lumen in fluid communication with first and second orifices of the two or more orifices. The indicator may be configured to transition from a first state to a second state for indication of utilization of the valve stem.

In some embodiments, the indicator comprises a recess included in the first portion and a detent included in the second portion, wherein the detent is received by the recess when the indicator transitions from the first state to the second state. In various embodiments, the valve stem changes from a first length to a second length when the indicator transitions from the first state to the second state.

In yet another aspect, the present disclosure relates to a method. The method may include one or more of exposing a valve stem to a valve well; and transitioning an indicator from a first state to a second state, wherein transition from the first state to the second state indicates exposure of the valve stem to the valve well.

In some embodiments, exposing the valve stem to the valve well comprises one or more of inserting the valve stem into a valve well, controlling flow of a fluid through the valve well with the valve stem, and removing the valve stem from the valve well:

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 1A and 1B illustrate various aspects of an exemplary valve assembly in conjunction with a valve well according to one or more embodiments disclosed hereby.

FIGS. 3A-3C illustrate an exemplary indicator in various states according to one or more embodiments disclosed hereby.

FIGS. 4A and 4B illustrate an exemplary indicator in various states according to one or more embodiments disclosed hereby.

FIGS. 5A and 5B illustrate various aspects of an exemplary valve assembly in conjunction with a valve well according one or more embodiments disclosed hereby.

FIGS. 7A-7D illustrate various aspects of an exemplary valve assembly according one or more embodiments disclosed hereby.

DETAILED DESCRIPTION

Figure 1B:
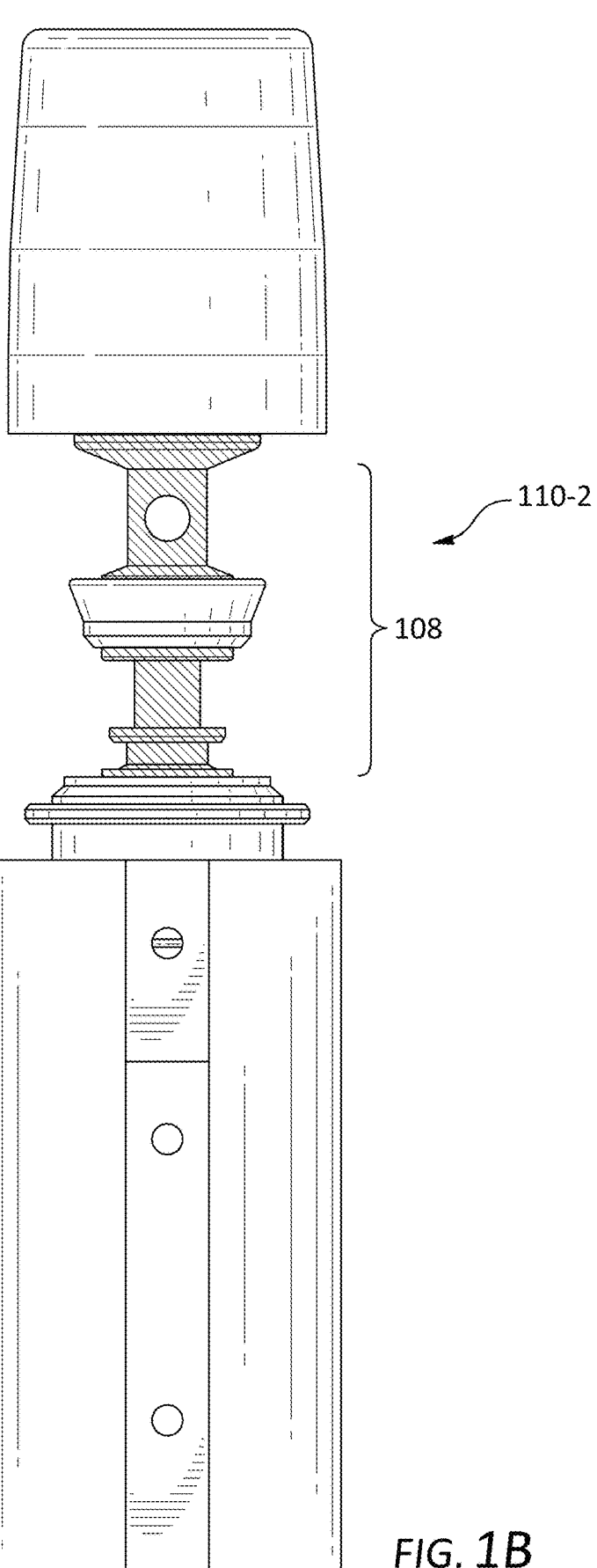

A medical cleaning valve (or cleaning valve) may be configured to provide cleaning functionality to air and water channels of an endoscope. In a first configuration, the cleaning valve may provide a continuous feed of air to both air and water channels in a handle and shaft of an endoscope, and through an air/water nozzle at the distal end of the endoscope. In a second configuration, the cleaning valve may feed water into the air channel in the handle and shaft of the endoscope, and through the air nozzle at the distal end of the endoscope. The cleaning valves (or valves) of the current disclosure are generally single-use devices (SUDs) and therefore disposable. Reusing SUDs that are not designs for reprocessing and reuse can result in unnecessary exposure to bacteria. Accordingly, many valves (or valve assemblies) disclosed hereby may be configured to transition from a first state to a second state for indication of utilization (e.g., prior utilization) of the valve with a valve well. In some embodiments, the transition from the first state to the second state may prevent reuse in of one or more valves disclosed hereby.

Further, the valve may be made from a limited number of parts and materials, e.g., to limit its cost, so that it may be economically disposable. For example, an interface member may seal an opening to the lumen of the valve. In another example, the valve may have a single elastomeric component, or spring cap. Additionally, cleaning valves may have a similar appearance to procedural valves. However, using a cleaning valve in place of a procedural valve may result in fluid flow through an incorrect endoscope channel, e.g., liquid being delivered through the air channel. Accordingly, one or more embodiments disclosed hereby may include cleaning valves with features and/or components that facilitate differentiating them from procedural valves.

It may be understood that the disclosure included herein is exemplary and explanatory only and is not restrictive. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." As used herein, the term "proximal" means a direction closer to a surface used by an operator for operating a valve (e.g., an interface member, a user interface, a button) and the term "distal" means a direction away from the surface used by an operator for operating a valve (e.g., a button). Although endoscopes are referenced herein, reference to endoscopes or endoscopy should not be construed as limiting the possible applications of the disclosed aspects. For example, the disclosed aspects may be used with duodenoscopes, bronchoscopes, ureteroscopes, colonoscopes, catheters, diagnostic or therapeutic tools or devices, or other types of medical devices. Additionally, although cleaning valves are referenced herein, reference to cleaning valves should not be construed as limiting the possible applications of the disclosed aspects. For example, the disclosed aspects may be used with a variety of medical valves for controlling the flow of fluids.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

FIGS. 1A and 1B illustrate various aspects of a valve assembly 100 in conjunction with a valve well 106 according to one or more embodiments of the present disclosure. The valve assembly 100 may include an interface member 102 and a valve stem 104 with an indicator 108 and an orifice 112-1. The valve assembly 100 and valve well 106 may be oriented with proximal end 105 and distal end 115. The valve stem 104 may include a lumen (now shown) connecting the orifice 112-1 to a second orifice (see e.g., orifice 712-2 in FIG. 7C). In some embodiments, FIGS. 1A and/or 1B may include one or more components that are the same or similar to one or more other components of the present disclosure. Further, one or more components of FIGS. 1A and/or 1B, or aspects thereof, may be incorporated into other embodiments of the present disclosure without departing from the scope of this disclosure. Embodiments are not limited in this context.

In one or more embodiments of the present disclosure, one or more components of the valve assembly 100 and/or valve well 106 may interoperate to facilitate transition of the indicator 108 from a first state 110-1 (see FIG. 1A) to a second state 110-2 (see FIG. 1B) to indicate utilization of the valve stem 104 with the valve well 106. For example, prior utilization of the valve stem 104 with the valve well 106 may comprise one or more of insertion of the distal end 115 of the valve assembly 100 into the proximal end 105 of the valve well 106, controlling the flow of fluid through the valve well 106 with the valve assembly 100, and removing the valve assembly 100 from the valve well 106. In some embodiments, the prior utilization may cause the transition from the first state 110-1 to the second state 110-2. For example, insertion of the valve stem 104 into the valve well and/or controlling the flow of fluid through the valve well 106 may cause indicator 108 transition from the first state 110-1 to the second state 110-2.

In several embodiments, the transition may comprise the indicator changing from a first color to a second color due to the indicator 108 of the valve stem 104 including a material that changes color when exposed to a fluid, such as water. Accordingly, the indicator 108 of valve stem 104 may transition from a first color to a second color when the valve stem 104 is exposed to a fluid, such as by controlling fluid flow through the valve well 106. Oftentimes, the indicator 108 may be a coating applied to one or more portions of the valve stem and/or interface member 102. In various embodiments, the first state 110-1 may include a pre-utilization state and the second state 110-2 may include a post-utilization state. In some embodiments, the transition may be a continuous change or a change in three or more discrete steps.

Figure 2A:
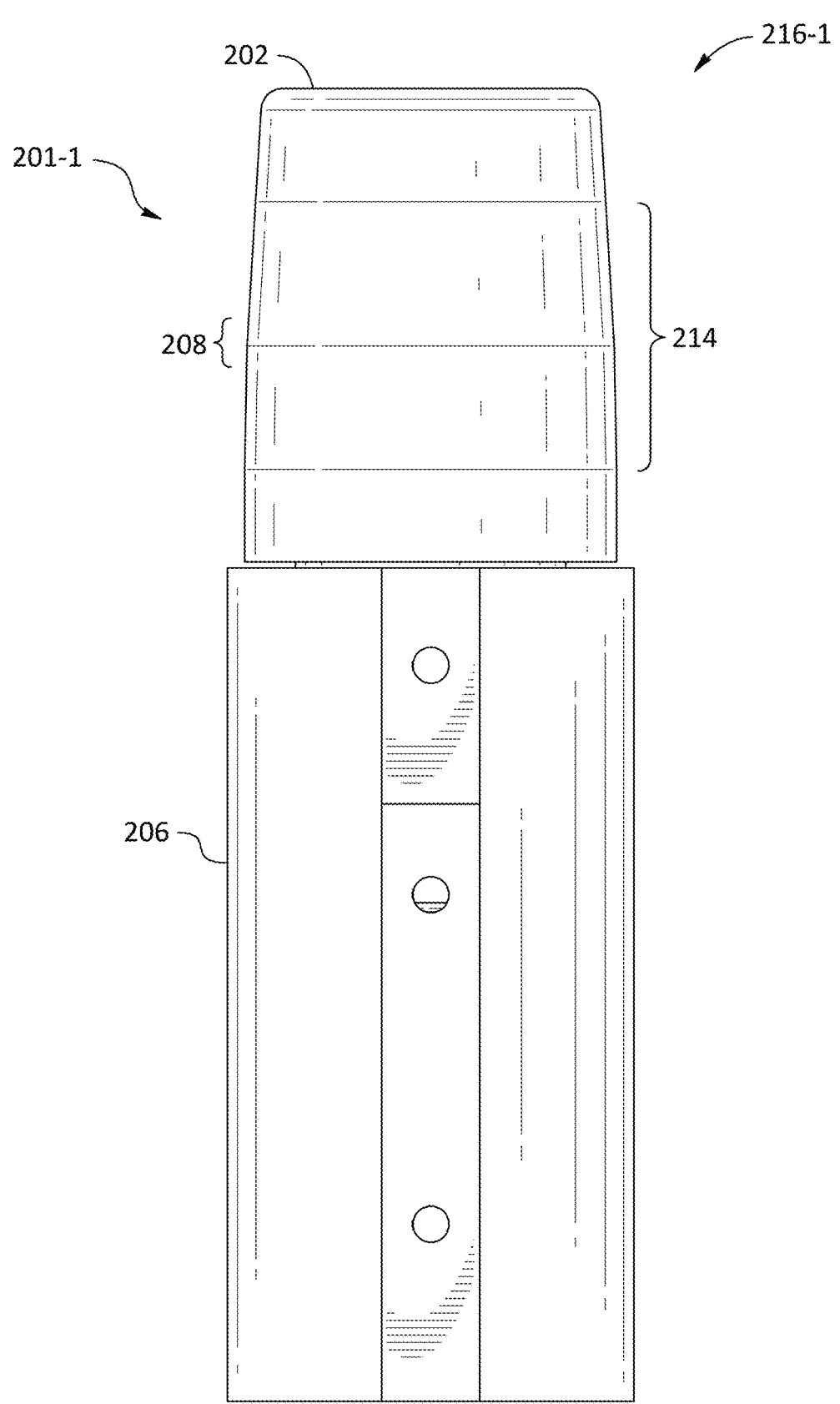
FIGS. 2A and 2B illustrate various aspects of an exemplary interface member in conjunction with a valve well according to one or more embodiments disclosed hereby.
Figure 2B:
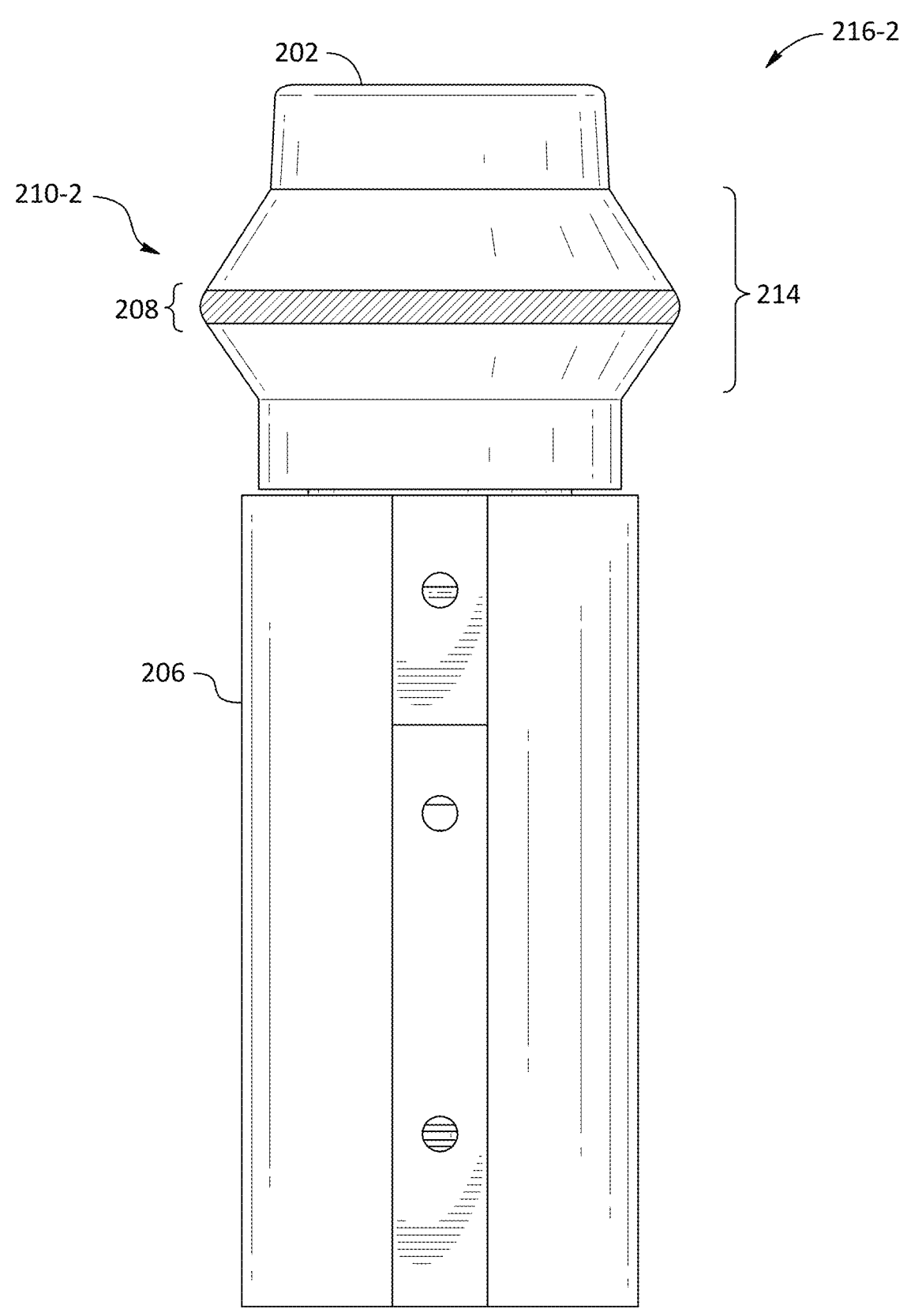

FIGS. 2A and 2B illustrate various aspects of an interface member 202 in conjunction with a valve well 206 according to one or more embodiments of the present disclosure. The interface member 202 may include an indicator in a first state 210-1, an elastic section 214. The interface member 202 may be coupled to a valve stem (not shown) disposed in the valve well 206. In several embodiments, the interface member 202 and the valve stem may comprise at least a portion of a valve assembly. In FIG. 2A, the interface member 202 is in a first configuration 216-1; and in FIG. 2B, the interface member 202 is in a second configuration 216-2. In some embodiments, FIGS. 2A and/or 2B may include one or more components that are the same or similar to one or more other components of the present disclosure. For example, interface member 202 may be the same as interface member 102. Further, one or more components of FIGS. 2A and/or 2B, or aspects thereof, may be incorporated into other embodiments of the present disclosure without departing from the scope of this disclosure. For example, the indicator 208 may be incorporated into interface member 102 without departing from the scope of this disclosure. Embodiments are not limited in this context.

In one or more embodiments of the present disclosure, various components of the valve assembly comprising interface member 202 may interoperate to facilitate transition of the indicator 208 from a first state 210-1 (see FIG. 2A) to a second state 210-2 (see FIG. 2B). In one or more such embodiments, an indicator 208 in the second state 210-2 may indicate utilization of the valve stem 104 with the valve well 106. For example, utilization of the valve stem with the valve well 206 may comprise one or more of coupling the interface member to the valve well, transitioning the interface member 202 from a first configuration 216-1 to a second configuration 216-2 insertion of the distal end 115 of the valve assembly 100 into the proximal end 105 of the valve well 106, controlling the flow of fluid through the valve well 106 with the valve assembly 100, and removing the valve assembly 100 from the valve well 106. In some embodiments, the utilization may cause the transition from the first state 110-1 to the second state 110-2. For example, insertion of the valve stem 104 into the valve well and/or controlling the flow of fluid through the valve well 106 may cause indicator 108 transition from the first state 110-1 to the second state 110-2.

In many embodiments, the transition may comprise the indicator changing from a first color to a second color due to the indicator 208 of the interface member 202 being stretched via a transition from configuration 216-1 to configuration 216-2. Accordingly, in various embodiments, indicator 208 may comprise a mechanochromatic film disposed on the elastic section 214. The mechanochromatic film may change colors due to flexing, stretching, tearing (see e.g., FIG. 4B). and/or bending of the indicator 208 resulting from the elastic section 214 flexing and/or stretching. The indicator 208 may be disposed on the illustrated portion of the elastic section 214 because that portion is subjected to the highest stresses on the elastic section 214. In some embodiments, the mechanochromatic material may be sprayed on. In various embodiments, the mechanochromatic material is a coating on an indicator component. In some embodiments entire components may be made out of or covered with mechanochromatic material. For example, the entire exterior of the interface member 602 may be coated with a mechanochromatic material.

In various embodiments, the elastic section 214 may function as a biasing member. For example, elastic section 214 may bias the interface member 202 (and the corresponding valve assembly) into the first configuration. In some embodiments, the walls of the elastic section 214 may have a varying in thickness and or other structures to bias interface member 202 into the first configuration 216-1. In some embodiments, the first configuration 216-1 may comprise a standby configuration and the second configuration 216-2 may comprise an actuated configuration. In several embodiments, the interface member 202 may couple with the valve well. In several such embodiments, the interface member 202 may exert a force against the valve well 206 to bias the interface member in the first configuration. In many embodiments, the second configuration 216-2 may cause fluid to flow through the valve well 206. On the other hand, the interface member 202 (and remainder of valve assembly) may be coupled to the valve well 206 in the first configuration 216-1 without causing fluid to flow through the valve well 206. In many embodiments, the interface member 202 may be displaced distally to transition from the first configuration 216-1 to the second configuration 216-2. Further, the distal displacement of the interface member 202 moves the valve stem distally within the valve well 206.

FIGS. 3A-4B illustrate various embodiments of indicators 308, 408 in various states 310-1, 310-2, 310-3, 410-1, 410-2 according to one or more embodiments of the present disclosure. The indicators 308, 408 may utilize color change to indicate utilization of the valve stem with a valve well. More specifically, the indicator 308 of FIGS. 3A-3C may include first, second, and third states 310-1, 310-2, 310-3. The first and third states 310-1, 310-3 may represent pre-utilization and post utilization states, respectively. In some embodiments, the second state 310-2 may represent a discrete state between the pre-utilization and post-utilization states. In other embodiments, the second state 310-2 may illustrate a point during a continuous transition between the colors of state 310-1 and 310-3. In some embodiments, FIGS. 3A-4B may include one or more components that are the same or similar to one or more other components of the present disclosure. Further, one or more components of FIGS. 3A-4B, or aspects thereof, may be incorporated into other embodiments of the present disclosure without departing from the scope of this disclosure. For example, the indicator 408 may be incorporated into one or more components of valve assembly 100 without departing from the scope of this disclosure. Embodiments are not limited in this context.

Some embodiments may include a polymer button or valve cap (e.g., interface member 202) with a film or blend of mechanochromatic material, which changes color when strain is induced in the material. Mechanical stresses in the mechanochromatic material alters the optical properties (absorption, emission, and reflection of light) which changes the materials color, temporarily or permanently. Many embodiments may utilize a permanent color change to indicate a SUD has been used long after the use. A thin mechanochromatic film (e.g., thin film) may be placed on a polymer to change its color as it is stretched. Accordingly, in several embodiments, the mechanochromatic film may be deposited on the elastic section 214.

Figure 5B:
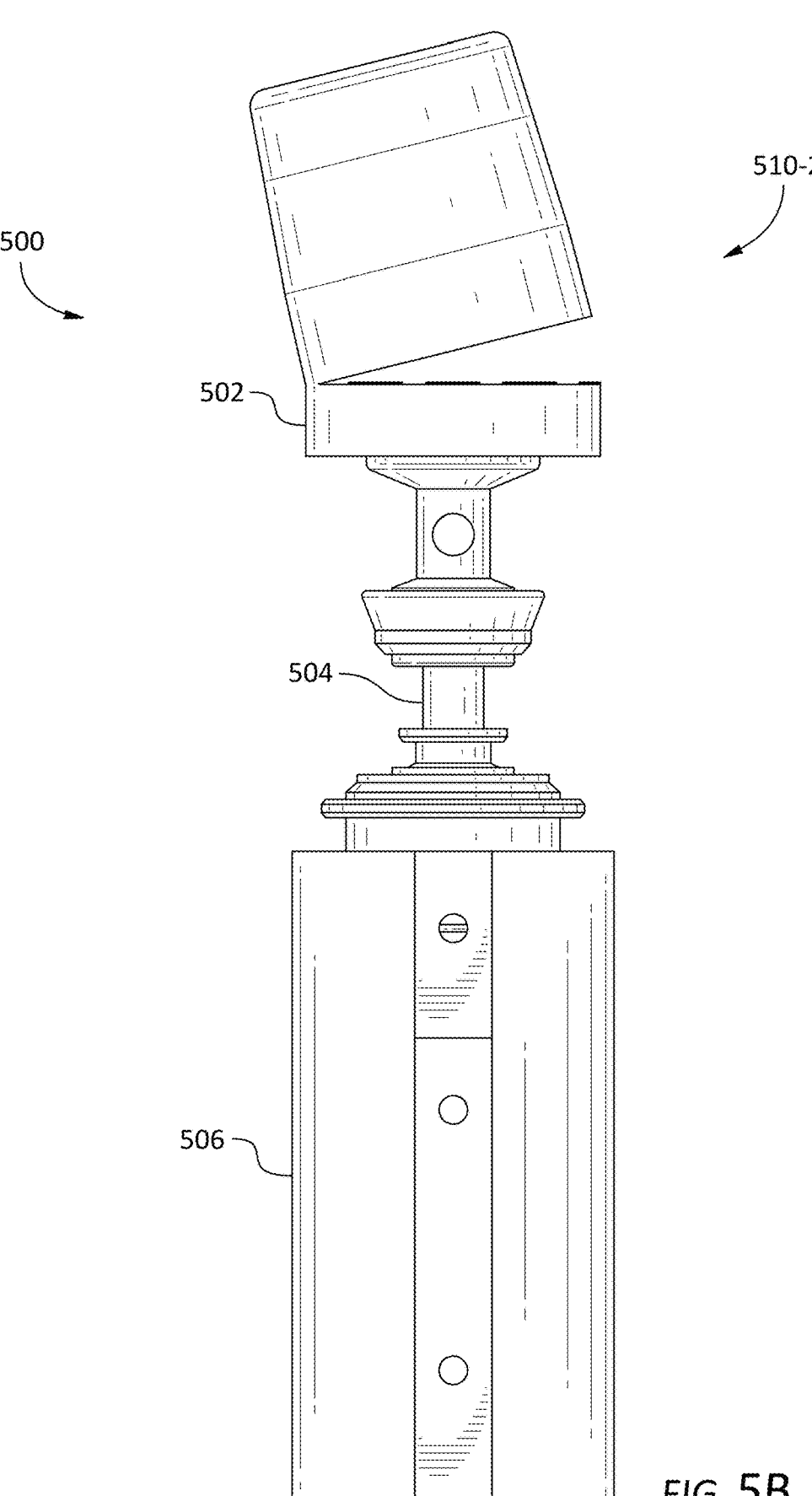

FIGS. 5A and 5B illustrate various aspects of a valve assembly 500 in conjunction with a valve well 506 according to one or more embodiments of the present disclosure. The valve assembly 500 may include an interface member 502 with a perforation 518 and a valve stem 504. In the illustrated embodiments, the perforation 518 may tear when the valve assembly 500 is removed from the valve well 506, thereby transitioning the valve assembly 500 from the first state 510-1 to the second state 510-2. The tear may indicate utilization of the valve stem 504 in the valve well 506 and the tear may prevent or limit the functionality of the valve assembly 500 in the second state 510-1. In one or more embodiments, the perforation 518 may include molded weak points. In other embodiments, the perforations 518 may be added through subtractive manufacturing. In some embodiments, FIGS. 5A and/or 5B may include one or more components that are the same or similar to one or more other components of the present disclosure. For example, valve stem 504 may be the same or similar to valve stem 104. Further, one or more components of FIGS. 5A and/or 5B, or aspects thereof, may be incorporated into other embodiments of the present disclosure without departing from the scope of this disclosure. For example, the perforation 518 may be incorporated into the interface member 102 or interface member 202 without departing from the scope of this disclosure. Embodiments are not limited in this context.

Figure 6A:
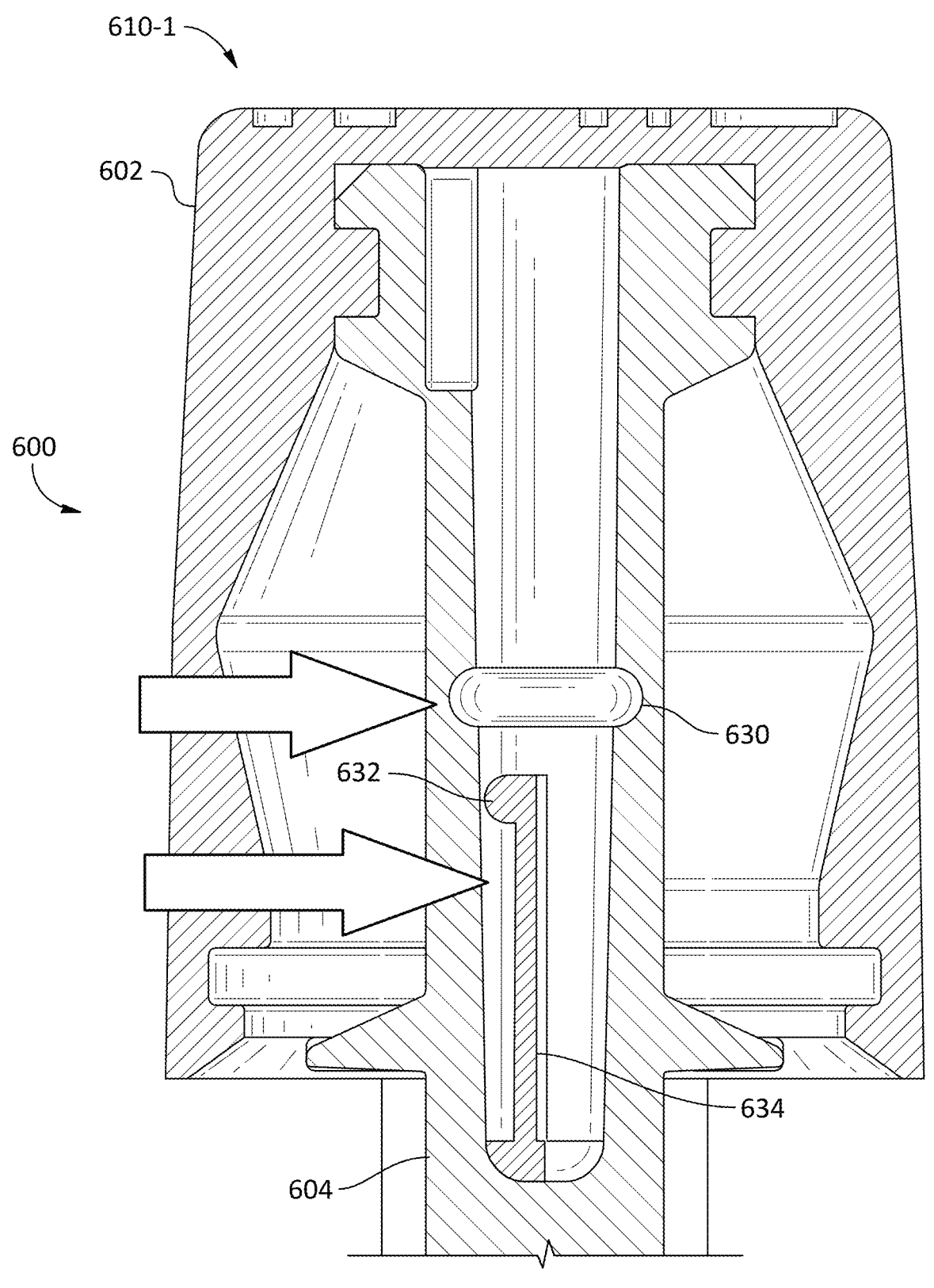
FIGS. 6A and 6B illustrate various aspects of an exemplary valve assembly according one or more embodiments disclosed hereby.
Figure 6B:
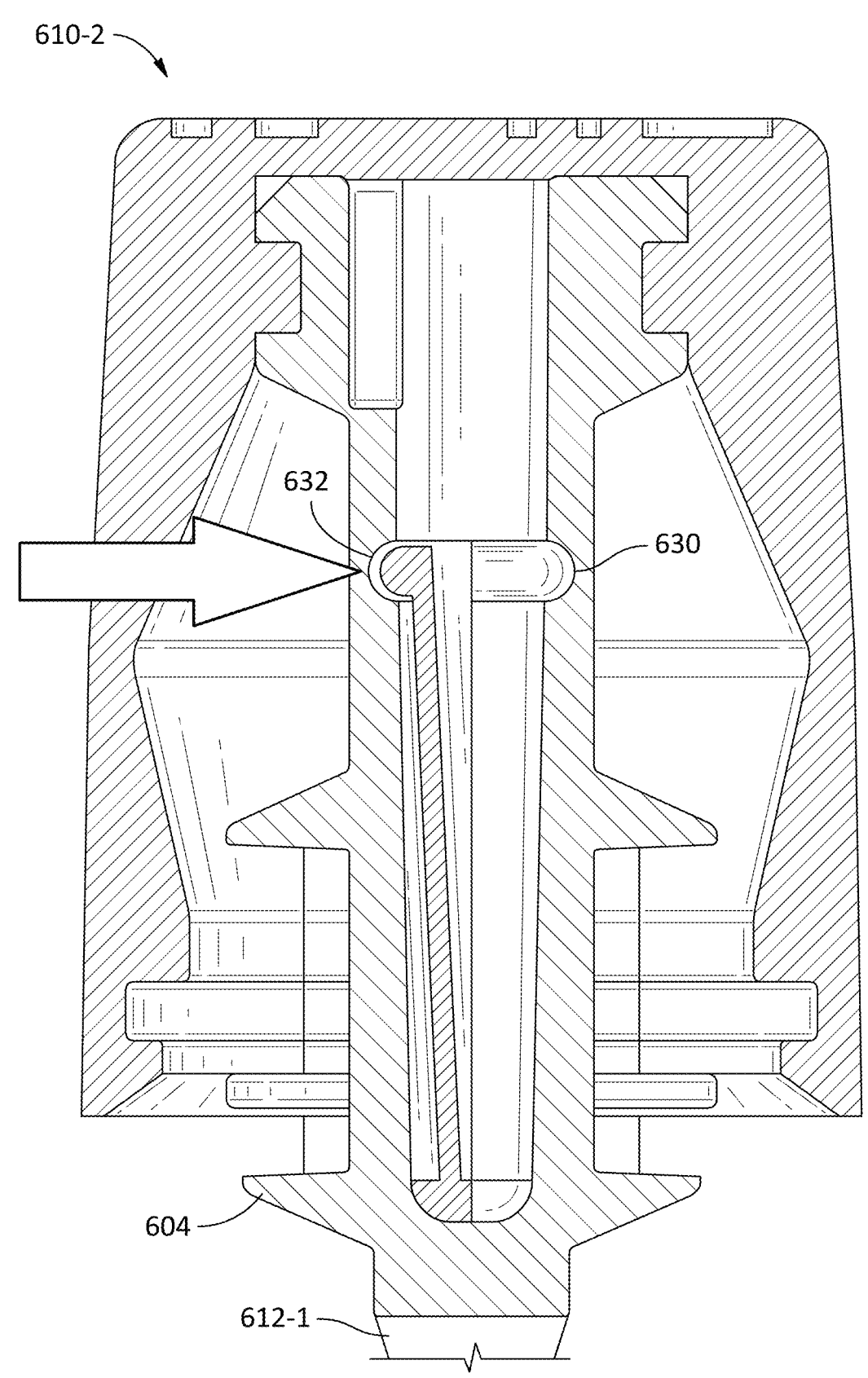

FIGS. 6A and 6B illustrate various aspects of a valve assembly 600 according to one or more embodiments of the present disclosure. The valve assembly 600 may include an interface member 602 coupled to a valve stem 604. The valve stem 604 may include a recess 630 and a detent 632 coupled to the end of a detent arm 634. In the illustrated embodiments, the recess 630, detent 632, and detent arm 634 may operate to transition the valve assembly into a second state 610-2 from a first state 610-1 in response to the interface member 602 be depressed to transition from a standby configuration to an actuated configuration. In many embodiments, a transition from the first state 610-1 to the second state 610-2 may render the valve assembly incompatible with a valve well. In some embodiments, FIGS. 6A and/or 6B may include one or more components that are the same or similar to one or more other components of the present disclosure. For example, valve stem 604 may be the same or similar to valve stem 104. Further, one or more components of FIGS. 6A and/or 6B, or aspects thereof, may be incorporated into other embodiments of the present disclosure without departing from the scope of this disclosure. For example, the recess 630, detent 632, and detent arm 634 may be incorporated into the valve assembly 100 without departing from the scope of this disclosure. Embodiments are not limited in this context.

In some embodiments, the recess 630, detent 632, and detent arm 634 function as an axe wedge splitting shaft embodiment. This embodiment may use two wedge shapes to increase the size of the interface member 602 to prevent interfacing onto the valve well and/or valve stem 604. For example, when the valve assembly is moved distally due to the interface member 602 being depressed, the shaft (e.g., arm 634) may split and prevent the interface member 602 coupling with a valve well. In some embodiments, one or more portions of the valve stem 604 may be perforated. In some embodiments, the top wedge attached to the outer cap assembly is a plastic, rubber, metal, or other harder material that is driven into the shaft wedge (e.g., via transitioning the valve assembly from a first configuration to a second configuration (see e.g., FIGS. 2A and 2B.

In some embodiments, the recess 630, detent 632, and detent arm 634 function as a detent elongating shaft. This embodiment may utilize an integrated detent to lengthen the valve assembly 600, rendering the valve assembly 600 incompatible with a valve well. The embodiment may utilize a male and inverse female configuration that when the device is removed from the valve well the male and female portions are mated (see e.g., detent 632 and recess 630 in FIG. 6B), lengthening the valve stem 604. This may prevent the valve assembly from being activated a second time. In some embodiments, when the valve assembly is actuated the male and female are mated effectively shortening the length of the valve stem 604. In some embodiments, the valve stem 604 may have one or more telescoping portions.

Figures 7C, 7D:
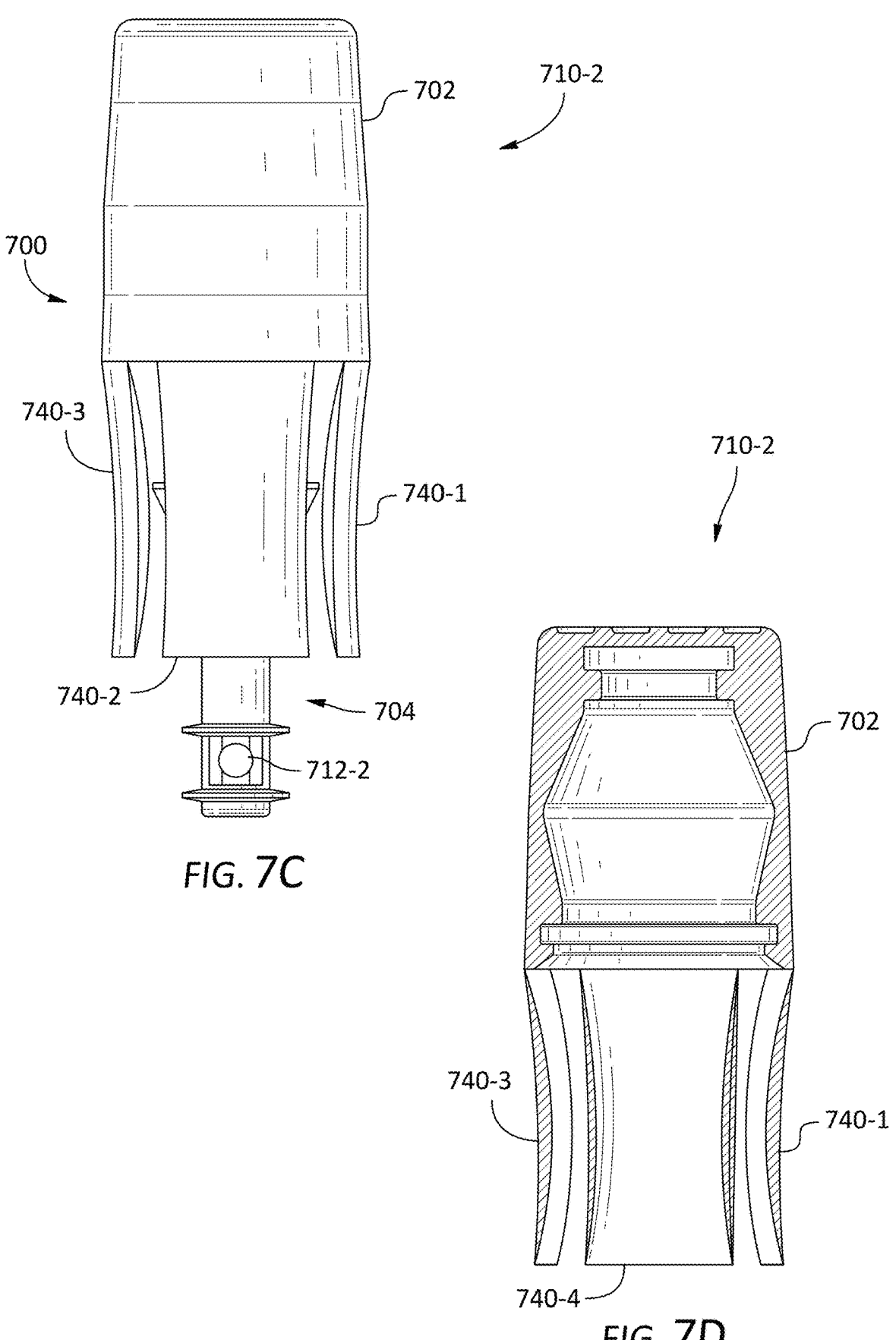

FIGS. 7A-7D illustrate various aspects of a valve assembly 700 according to one or more embodiments of the present disclosure. Referring specifically to FIG. 7A, a perspective view of an interface member 702 with radial legs 740-1, 740-2, 740-3, 740-4 is illustrated. FIG. 7B illustrates a cross-sectional view of interface member 702 with radial legs 740-1, 740-3 and elastic section 714. FIG. 7C illustrates valve assembly 700 with the interface member 702 coupled to valve stem 704. Further, a second orifice 712-2 of valve stem 704 is illustrated. FIG. 7D illustrates a cross-sectional view of interface member 702. Additionally, interface member 702 is in a first state 710-1 in FIGS. 7A and 7B, but in a second state 710-2 in FIGS. 7C and 7D. In some embodiments, FIGS. 7A-7D may include one or more components that are the same or similar to one or more other components of the present disclosure. For example, valve stem 704 may be the same or similar to valve stem 104. Further, one or more components of FIGS. 7A-7D, or aspects thereof, may be incorporated into other embodiments of the present disclosure without departing from the scope of this disclosure. For example, the radial legs 740 of interface member 702 may be incorporated into the interface member 202 without departing from the scope of this disclosure. Embodiments are not limited in this context.

In the illustrated embodiments, radial displacement of the elastic section 714 due to compression of the interface member 702 may cause a first end of the radial arms to detach from the interface member 702. In many embodiments a second end of the radial arms pivots with respect to the interface member 702, resulting in the first end of the radial arms inverting with the second end of the radial arms when the interface member 702 transitions from the first state 710-1 to the second state 710-2.

In several embodiments, the radial arms 740 may comprise winglets or flaps added to the outside of the interface member with a living hinge on the second end. The first end may be perforated, include a molded weak point, and/or a snap connection with the interface member 702. When the interface member 702 is actuated (e.g., transitions configurations), the action of the elastic section expanding radially may tear the perforated edge of the winglets. The winglets may then be free to actuate on their living hinges. When the valve assembly 700 is removed from a valve well the winglets would vias to the lowest position and cover portions of the valve stem 704 (see e.g., FIG. 7C). In many embodiments this transition from state 710-1 to state 710-2 may render the valve assembly 700 incompatible with valve wells, such as by blocking reinsertion.

In many embodiments, one or more components and/or features disclosed hereby may be used to differentiate cleaning valves from procedural valves. For example, radial legs 740 may differentiate valve assembly 700 from procedural valve assemblies. In another example, the interface member 702 may include one or more features for distinction, such as raised surfaces, colors, warning labels, and the like. For instance, the proximal end of interface member 702 includes raised surfaces in the form of a warning label.

This application relates to, and incorporates by reference in their entireties for all purposes, U.S. patent application Ser. No. 16/868,325, titled "Devices, Systems, Methods, and Designs for Medical Cleaning Valves, filed May 6, 2020.

This application relates to, and incorporates by reference in their entireties for all purposes, U.S. patent application Ser. No. 16/868,329, titled "Devices, Systems, and Methods for Medical Cleaning Valves, filed May 6, 2020.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method disclosed hereby without departing from the concept, spirit, and scope of the disclosure.

What is claimed is:

1. A valve assembly, comprising:
a valve stem, the valve stem including two or more orifices and a lumen in fluid communication with first and second orifices of the two or more orifices; and
an indicator configured to transition from a first state to a second state in response to utilization of the valve stem, the second state precluding reuse of the valve assembly in a valve well of an endoscope.

2. The valve assembly of claim 1, wherein the indicator is disposed on the valve stem.

3. The valve assembly of claim 1, further comprising:
an interface member removably couplable with the valve stem, and
wherein the interface member comprises an elastic section and the indicator is disposed on a portion of the elastic section.

4. The valve assembly of claim 3, wherein the indicator is disposed on the interface member.

5. The valve assembly of claim 3, wherein the elastic section comprises a biasing section configured to bias the valve stem into a predetermined position in the valve well.

6. The valve assembly of claim 3, wherein the indicator comprises a radial leg disposed on the interface member, the radial leg including first and second ends.

7. The valve assembly of claim 1, wherein the utilization of the valve stem comprises insertion of the valve stem into the valve well and removal of the valve stem from the valve well.

8. The valve assembly of claim 7, wherein the indicator transitions from the first state to the second state when the valve stem is removed from the valve well.

9. The valve assembly of claim 7, wherein the indicator comprises a perforation that separates to transition from the first state to the second state when the valve stem is removed from the valve well.

10. The valve assembly medical device of claim 9, wherein the perforation comprises a radial perforation.

11. The valve assembly of claim 1, wherein the utilization of the valve stem includes exposing the indicator to a liquid.

12. A method, comprising:
utilizing a valve stem of an endoscope valve assembly in a valve well of an endoscope; and
transitioning an indicator of the endoscope valve assembly from a first state to a second state in response to utilizing the valve stem in the valve well, the second state precluding reuse of the endoscope valve assembly.

13. The method of claim 12, wherein utilizing the valve stem in the valve well comprises one or more of inserting the valve stem into the valve well, controlling flow of a fluid through the valve well with the valve stem, and removing the valve stem from the valve well.

14. The method of claim 12, wherein utilizing the valve stem comprises inserting the valve stem into the valve well and removing of the valve stem from the valve well.

15. The method of claim 14, wherein the indicator transitions from the first state to the second state when the valve stem is removed from the valve well.

16. The method of claim 12, wherein transitioning the indicator from the first state to the second state includes separating a perforation when the valve stem is removed from the valve well.

17. The method of claim 16, wherein the perforation comprises a radial perforation.

18. The method of claim 12, wherein transitioning the indicator of the endoscope valve assembly from the first state to the second state includes exposing the indicator to a liquid.

19. A medical device, comprising:
an interface member;
an indicator; and
a valve stem to which the interface member is couplable, and
wherein the indicator is configured to transition from a first state indicating that the valve stem has not yet been utilized to a second state in response to utilization of the valve stem, the second state precluding reuse of the medical device.

20. The medical device of claim 19, wherein the indicator is disposed on the valve stem.

* * * * *